United States Patent [19]

Farr et al.

[11] Patent Number: 5,341,822
[45] Date of Patent: Aug. 30, 1994

[54] BANDAGE CUTTER AND REMOVER

[76] Inventors: John A. Farr, P.O. Box 158, New Creek, W. Va. 26743; R. Dwight Leatherman, Rte. #5 Box 171, Keyser, W. Va. 26726

[21] Appl. No.: 51,698

[22] Filed: Apr. 26, 1993

[51] Int. Cl.$^5$ .......................... A61B 19/00; B26B 5/00
[52] U.S. Cl. ...................................... 128/898; 30/294; 30/329; 606/167
[58] Field of Search ................. 30/286, 289, 294, 321, 30/335, 314, 315; 606/166, 167, 172; 128/898

[56] References Cited

U.S. PATENT DOCUMENTS

| | | | |
|---|---|---|---|
| 3,610,246 | 10/1971 | Salmon | 606/167 |
| 3,751,806 | 8/1973 | Patrick | 30/294 |
| 4,604,804 | 8/1986 | Sparks | 30/294 |
| 5,122,152 | 6/1992 | Mull | 30/294 |

Primary Examiner—Eugenia Jones
Assistant Examiner—Hwei-Siu Payer
Attorney, Agent, or Firm—John W. Adee

[57] ABSTRACT

There is disclosed an instrument for cutting bandages which has a handle and a base guide foot section. The base guide foot has a nose section which extends past the edge of a blade positioned within the instrument. The base guide unit has an enlarged portion on its bottom area which permits the instrument to ride on only a small area and be pivoted on the area when in use. In one version the instruments has a removable blade unit which can be installed and removed without being contacted by the installer thereby reducing possibility of contamination.

9 Claims, 1 Drawing Sheet

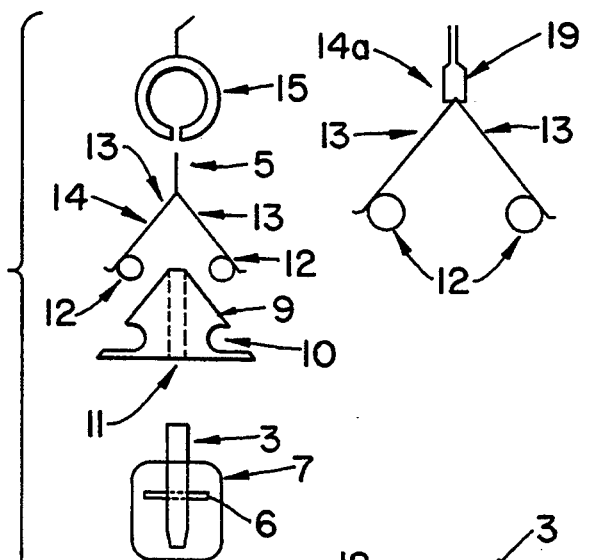
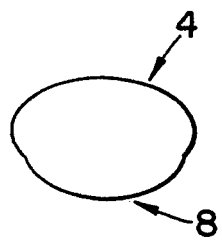
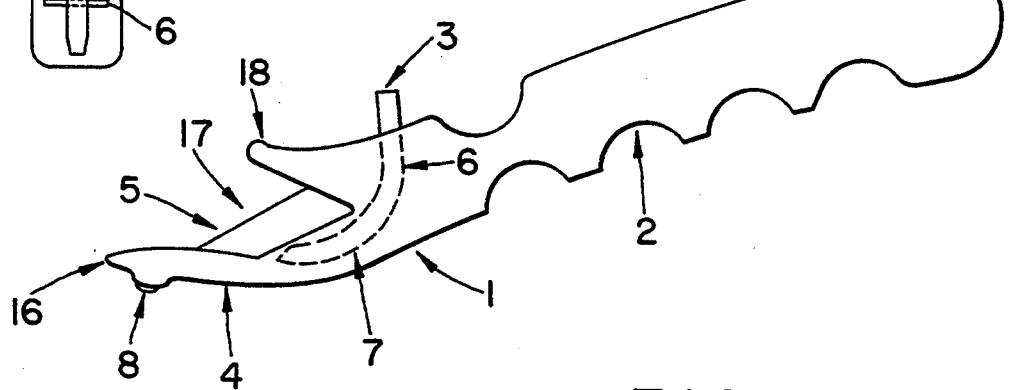
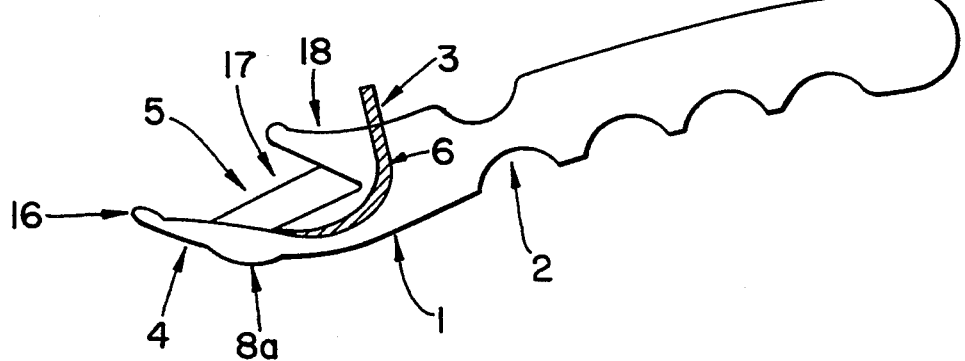
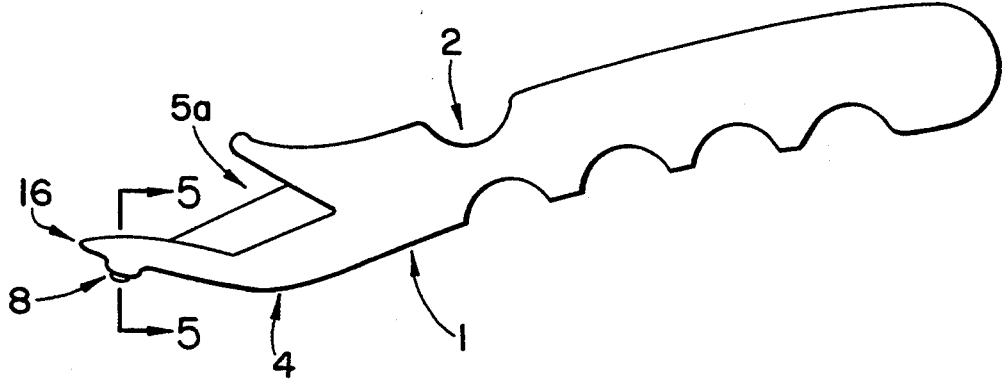

BANDAGE CUTTER AND REMOVER

FIELD OF INVENTION

This invention relates to a medical instrument for removing bandages from a body, and particularly a human body.

BACKGROUND OF THE INVENTION

Mr. Farr, one of the inventors, has a medical condition which requires his legs be bandaged. Regularly the old bandages are removed and new bandages applied. The doctors and nurses use a pair of scissors to remove the bandages and instructed him how to remove the bandages himself. He found the use of scissors to be tedious and sometimes painful. Upon inquiry, he was informed by both doctors and nurses that scissors were the only instrument they were aware of suitable for removal. He thought there should be a better way.

Mr. Farr conceived of the idea of using a razor blade, but finding a way to make it safe proved difficult. He discovered there was a device for removing bandages from horses legs. The device consisted of two plastic handles glued together with a blade clamped between them. There is an extended portion, with a nose, in front of the blade for lifting the bandage to start the cut.

It was found the device would remove the bandages but the doctor objected to the device on several grounds including, the device could not be sterilized, also while satisfactory for the tough skin of a horses leg the device was unsatisfactory for removing bandages from a human, particularly if there were sore or tender portions under the bandages, another objection was the blade was not removable, further the handle was so shaped that manipulating the device would be difficult. The doctor informed Mr. Farr the device would be a great benefit to doctors, nurses and patients alike if he could invent a device which overcome these objections. Mr. Farr and Mr. Leatherman have accomplished this task.

SUMMARY OF THE INVENTION

The present invention described and disclosed herein comprises an improved apparatus for removing bandages from human body parts. The apparatus consists of a handle, a guide foot section and a blade positioned between the guide foot section and the handle. The guide foot section has a slightly enlarged area usually, but not necessarily, near the end of the nose of the guide foot section which functions as a pivot for the instrument. The handle and guide foot join together in the same plane and form an angle at a point below the blade. Preferably this angle is 10 to 45 degrees but angles outside this range are usable. The angled area formed by the handle and guide foot can be used as a pivot point but is less desirable than using an enlarged area as later described. Placing finger grips on the bottom of the handle will improve the grip but are not necessary in normal use. The handle may be made up of two outer parts with a tang in between but it is more practical to make it in one piece.

There are two version of the invention. In one the blade is removable and the entire apparatus can be repeatedly sterilized by methods in common practice such as boiling in water or soaking in alcohol. The preferred material of construction is stainless steel, however other materials which are resistant to heat and/or sterilizing baths are usable in the invention. Means are provided to hold the blade tight while in use. The means could be an internal spring which is retracted in the handle, a tension puller could be mounted on the handle or a screw could be used to hold in the blade. One skilled in the art could think of other means. However the inventors have devised a blade release lever means mounted either beside the handle or within the handle which when pushed forward allows a blade unit assembly to be inserted and locked into a cavity within the handle and guide foot. This blade release lever means ejects the blade unit assembly when pulled backward. As will be explained later, the blade unit assembly can be inserted and removed without being touched, Thereby considerably reducing the chance of contamination of the user.

In the second version the entire apparatus with the exception of the blade is made of plastic which can be sterilized and sealed by the manufacture in well know manners. The blade is sealed in the plastic handle and guide foot section. This device can be made at a reasonable cost and is intended to be disposed of after one use. The enlarged section on the guide foot is the same as described in the first version. The blade can be held in place by being sealed between the handles or the blade can be sealed by gluing or by fusing with the plastic.

BRIEF DESCRIPTION OF THE DRAWINGS

For a more complete understanding of the invention and the advantages thereof reference is now made to the following description taken in conjunction with the accompanying drawings in which like numerals refer to like parts and those followed by an a refer to alternative parts.

FIG. 1 illustrates a bandage cutter having a removable blade and a blade release lever in the interior of the handle.

FIG. 2 illustrates an exploded view of a blade assembly, blade lock and a frontal view of the blade release lever.

FIG. 2A illustrates a modification of the blade assembly of FIG. 2.

FIG. 3 illustrates a bandage cutter similar to that in FIG. 1 except the blade release lever is on the outside of the handle.

FIG. 4 illustrates a disposable bandage cutter having a fixed blade.

FIG. 5 illustrates a view through 5—5 of FIG. 4 but also applicable to FIG. 1 and FIG. 3 and shows the enlarged area of the base guide foot.

DETAILED DESCRIPTION OF THE PREFERRED EMBODIMENTS OF THE INVENTION

FIG. 1, FIG. 3 and FIG. 4 have in common an elongated handle 1 with optional finger and thumb grips 2, and an elongated base guide foot 4. The handle 1 and guide foot 4 are joined together in the same plane and their bottom portions form an angle with each other which is preferably 10 to 45 degrees but angles outside this range are usable. A mouth section 17 is formed by the upper portion of the guide foot and an extension 18 of the handle 1. A cavity 7 is formed in the mouth section and within the upper portion of the guide foot 4 and the front portion of the handle 1. A blade 5 is shown in the cavity 7. An enlarged area 8 is formed near the nose end 16 of the guide foot. Alternatively the enlarged area may be placed just back of the blade edge as shown at 8a in FIG. 3. The enlarged area should be long enough not to provide a knife edge and not long enough to form an unnecessary drag on the skin. For example the enlarged area should be at least ¼" long to minimize cutting into the skin, while over 5/8" long would give excessive drag. In width, as shown in FIG. 5, the enlarged portion is rounded and is less than the width of the base guide foot 4. Normally the handle and guide foot 4 including the nose end are constructed in one piece.

Referring now specifically to FIG. 1 and FIG. 2 there is shown cavity 7 formed within the handle and guide foot 4. FIG. 2 is looking diagonally downward into the mouth of FIG. 1 with the blade removed. The cavity contains the blade release lever 3 which is held in place by a pin 6. Positioned above the blade release lever 3 is a fixed blade base 9, this is shown in larger scale than the cavity to permit greater detail, the fixed blade base 9 has notches 10 in its lower area for locking the blade unit in place and a passage 11 which permits the blade release lever 3 to contact the blade unit 14. The blade unit 14 has a blade 5 shown at the top and also shown in FIGS. 1 and 3. Two inverted V-shaped legs 13, also referred to as saddle shaped, are fastened to the blade at the top and a locking element which may be cylinder shaped for example is fastened to the opposite end of each leg. These elements are sized to fit snugly within the notches 10 of the fixed blade base 9 and the upper part of the fixed blade base 9 has sides slanted inwardly toward the top to fit snugly within the V or saddle shaped legs 13 of the blade unit 14. The blade unit 14a of FIG. 2A differs from blade unit 14 in that a slotted blade holder 19 is provided so the blade may be replaced and the blade unit used again after being sterilized. In this instance it is preferable the entire unit 14a be made of stainless steel but other metals and plastics can be used as long as they will withstand temperature of boiling water and/or withstand being in a bath of sterilizing agent such as alcohol for several hours. On the other hand, the legs and locking elements of blade unit 14 could be made of less costly materials since it is intended this unit will be discarded after use.

A blade protective cover or cap is designated by 15. However, the function of this cover is not restricted to protecting the blade in the normal manner. When ready to insert the blade unit 14 or 14a into the cavity 7, the cap 15 is gripped between the thumb and fingers or by a tong tool and pushed into the cavity 7 and over the blade base 9 until the locking elements 12 lock into the notches 10. The cap is then removed and the bandage cutter 1 is ready for use with a sterile blade unit installed. When using blade unit 14a, the cap can be replaced on the blade for removing the blade from the blade unit 14a without having to touch the blade.

As illustrated in FIG. 3 the blade release lever can be mounted on the side of the body. In this instance, the blade release lever 3 is curved inward to fit under the blade unit. This could also be made with an extension from the release mechanism to a position under the blade. This arrangement has the advantage of being less costly to manufacture than the instrument of FIG. 1, but considering the overall advantages, the arrangement as illustrated and described in regard to FIG. 1 is preferred by the inventors. Also illustrated in FIG. 3 is the enlarged area 8a on the base guide foot 4. In this embodiment the enlarged area is placed back of the cutting edge of the blade. By having the enlarged area in this position, the bandage is severed ahead of the enlarged area thus relieving the pressure of the bandage on the body part contacted.

FIG. 4 illustrates a bandage cutter instrument which is intended to be packaged in a sterile condition and be discarded after one use. The handle, guide foot and enlarged area are the same as those of FIG. 1 and FIG. 3 except the parts may be constructed of lower cost materials than those used in the cutters intended for reuse. The blade 5a is fixed in the cutter, therefore no blade release lever is needed. Thus further reducing the cost of the bandage cutter instrument.

OPERATION OF THE INVENTION

In operation, referring to FIG. 1, the blade release lever 3 is pushed forward there by recessing the lower part of the blade release lever into the cavity 7. A sterile blade unit 14 is gripped by cap 15 and pushed into the cavity 7 until it locks into the fixed blade base 9. The user then places the nose end 16 of the base guide foot under the bandage. Upward pressure on the handle raises the instrument off the skin except for a portion of the enlarged area 8. This permits the instrument to be manipulated around sensitive areas as the user moves the instrument forward. The handle can be moved from one side to the other with very little drag or pressure on the skin. After the bandage has been severed the bandage cutter is turned upside down over a disposal. The blade release lever is pulled toward the rear of the handle. This ejects the blade unit into the disposal. The instrument is then ready to be sterilized for the next use.

When using the blade arrangement of FIG. 2A the blade is inserted in the slots of blade holder 19 using the cap 15. The blade unit is then inserted in the manner described for FIG. 2. After use the cap is replaced over the blade. The blade is then removed and the blade and cap disposed of. The blade unit can then be ejected directly into a sterilizing bath if desired.

When the enlarged area is behind the blade edge as shown in FIG. 3 then an upward pressure rather than a downward pressure is used to pivot the instrument on the enlarged area for cutting the bandage, and moving the handle from side to side in order to guide the nose section under the bandage.

The bandage cutter of FIG. 4 is removed from a container in a sterile condition. The cutter is manipulated in the same manner as described in regard to FIG. 1 or FIG. 3 depending on whether the enlarged portion is in front of the blade edge or behind the blade edge.

Although the description above contains many specificities, these should not be construed as limiting the scope of the invention but as merely providing illustration of some of the presently preferred embodiments of this invention.

Thus, the scope of the invention should be determined by the appended claims and their legal equivalents rather than by the examples given.

We claim:

1. An instrument for cutting bandages comprising an elongated handle, a guide foot elongated in the same direction as the handle and constructed at an angle to said handle, a blade within said handle and guide foot, a pivot area on the lower part of said guide foot, a nose end on said guide foot, said pivot area including an enlarged area on the lower part of said guide foot between the blade and the nose end constructed to contact the body from which a bandage is to be cut, thereby allowing the operator of said instrument to maneuver the guide foot under a bandage with only a minimal area of said instrument contacting a body part from which the bandage is being removed.

2. The instrument of claim 1 wherein the blade is permanently fixed in the instrument.

3. A bandage cutter constructed of a material which can be repeatedly sterilized, comprising an elongated handle, an elongated guide foot, a mouth formed by the handle and upper part of the guide foot, a cavity in said mouth, a blade ejector means in said cavity, said blade ejector means extending externally of said elongated handle, a fixed blade base in said cavity, said fixed blade base having a passageway through which the blade ejector means travels, notches in said fixed blade base for receiving corresponding elements of a blade unit which snap into said notches and hold the blade unit in place whereby the blade unit can be inserted and removed from the bandage cutter.

4. The bandage cutter of claim 3 wherein said fixed blade base is shaped with inwardly slanted sides toward the top so legs of the blade unit fit snugly over said fixed blade base.

5. The bandage cutter of claim 3 in which said blade ejector means is fastened centrally of said handle and when an externally extending means of the ejector means is pushed toward the cavity the blade ejector means recesses into said handle, then when the extending means is pulled away from the cavity the blade ejector means travels through the passageway in the fixed blade base and contacts the blade unit for removing said blade unit.

6. The bandage cutter of claim 3 further including a bottom on said guide foot, an enlarged area on said bottom which permits the bandage cutter to be maneuvered when in use.

7. In combination, a blade unit and a bandage cutter instrument, said blade unit having a blade, legs fastened to said blade and spread to form a saddle shape, locking elements on the end of each leg opposite the blade, and a cap on said blade; said bandage cutter instrument being constructed of a material capable of being repeatedly sterilized and having a handle joined at an angle with a guide foot section, said guide foot section having an enlarged area on its bottom and a nose section, said instrument having a mouth and a cavity formed in said mouth between said handle and said guide foot section, said cavity having a blade base fixed therein, said blade base being shaped to fit snugly between the legs of said blade unit, said blade base having notches in which the locking elements of said blade unit fit, said blade base having a passageway centrally thereof through which a blade ejector passes downward to permit insertion of the blade unit and passes upward to eject the blade unit, said blade ejector being positioned central of the handle and having a portion extending above the top of the handle whereby when the portion of the ejector extending externally of the top of the handle is pushed forward, the blade unit can be pushed into the cavity and over the blade base until the blade unit fastens in place over the blade base, and after use, the ejector is pulled backward to eject the blade unit from the cavity.

8. The combination of claim 7 wherein the bandage cutter instrument is constructed of stainless steel.

9. A method for cutting a bandage comprising the steps of selecting a cutter having a handle, a guide foot, a mouth with a cavity and a blade ejector in said cavity, selecting a sterile blade unit having a blade, a cap for said blade, and legs including means to lock said blade unit into said cutter; holding the blade unit by the cap and pushing said cap into said cutter mouth until it locks in place within the cavity, providing a nose end on said guide foot and providing an enlarged area on the bottom of said guide foot near the nose end, placing the nose end under the bandage, pushing downward on the handle until the cutter rests only on the enlarged area, then moving the instrument forward to move the blade into the bandage, and pivoting the cutter from side to side to guide around tender or sore parts of a body, continuing the movements until the bandage has been severed; turning the bandage cutter instrument over a disposal and engaging said blade ejector to eject said blade unit, thereby minimizing chances of contamination.

* * * * *